United States Patent [19]

Zdrodowski

[11] 4,004,884
[45] Jan. 25, 1977

[54] TIME DIVISION METERING SYSTEM

[75] Inventor: Joseph John Zdrodowski, Nutley, N.J.

[73] Assignee: Hoffmann-La Roche Inc., Nutley, N.J.

[22] Filed: July 2, 1976

[21] Appl. No.: 702,242

[52] U.S. Cl. .................................. 23/259; 137/88; 137/624.12
[51] Int. Cl.[2] .................... G01N 1/18; G01N 31/08
[58] Field of Search ............ 23/230 R, 253 R, 259, 23/292; 137/624.12, 88

[56] References Cited
UNITED STATES PATENTS

| | | | |
|---|---|---|---|
| 3,230,048 | 1/1966 | Skeggs | 23/230 X |
| 3,488,154 | 1/1970 | Hronas | 23/230 R |
| 3,557,077 | 1/1971 | Brunfeldt et al. | 23/259 X |
| 3,846,075 | 11/1974 | Cioffi | 23/259 X |

*Primary Examiner*—R.E. Serwin
*Attorney, Agent, or Firm*—Samuel L. Welt; George M. Gould

[57] ABSTRACT

An improved system for metering a plurality of fluids is described. The instant system utilizes time division switching in flow valves to provide accurate metering of a plurality of fluids from individual reservoirs.

7 Claims, 3 Drawing Figures

TIME DIVISION METERING SYSTEM

BACKGROUND OF THE INVENTION

A large number of chromatographic and analytical systems require the use of highly accurate amounts of a number of fluids for optimal operation. Such systems include, for example, fluoresence meters wherein buffers and reagents must be provided in highly controlled amounts. Alternatively, chromatographic systems require controlled pH gradients in order to effectuate proper elution of materials from the column.

BRIEF DESCRIPTION OF THE INVENTION

The present invention relates to a novel time division metering system which is utilized to provide highly accurate multifluid metering from a plurality of independent reservoirs. The basis for the instant invention involves the time division switching of flow valves leading from each of the aforesaid reservoirs.

Figure 1:
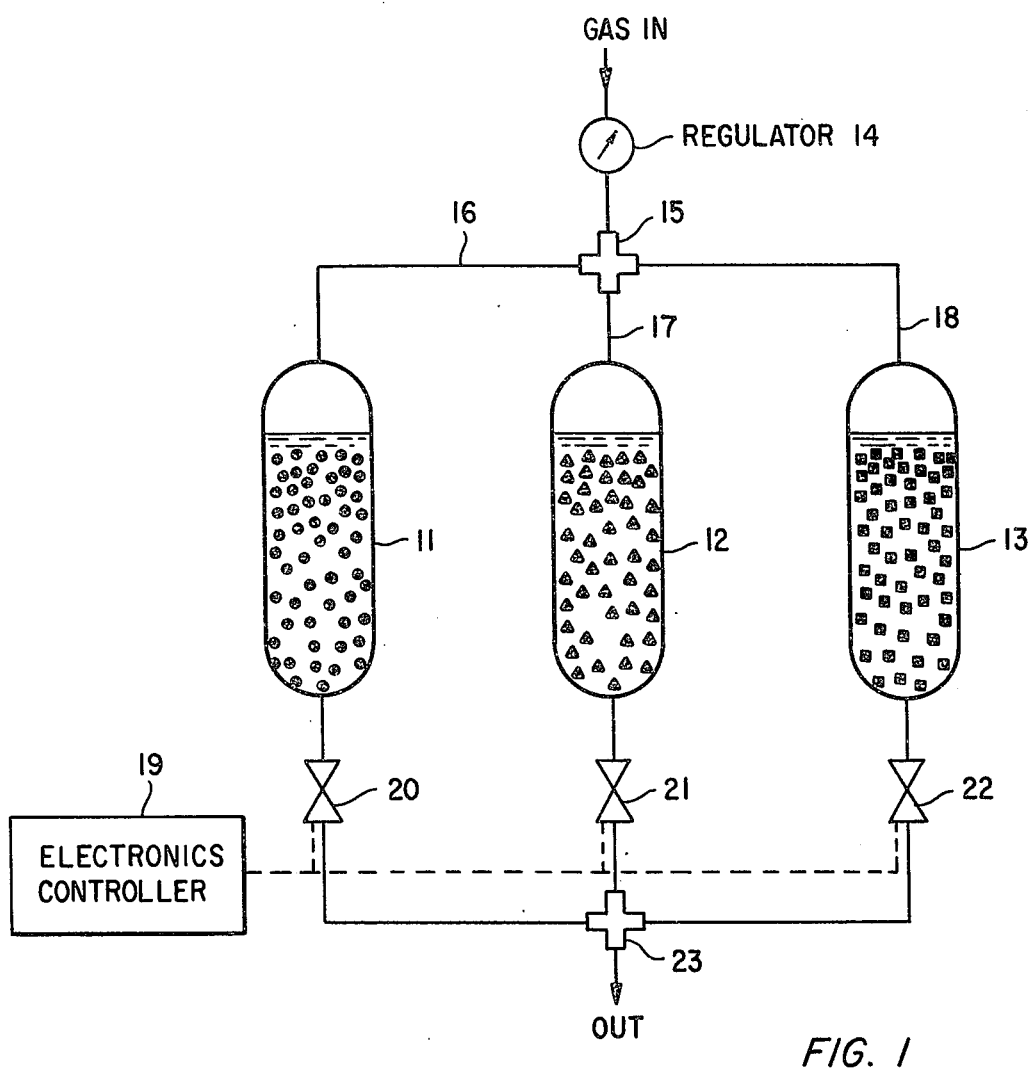
Figure 2:
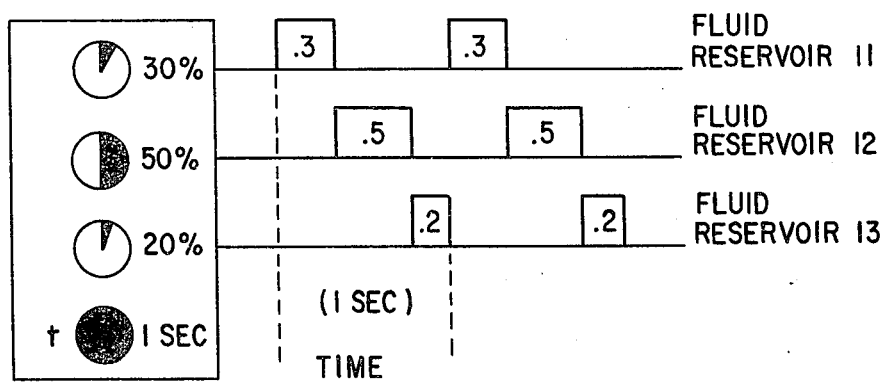
Figure 3:
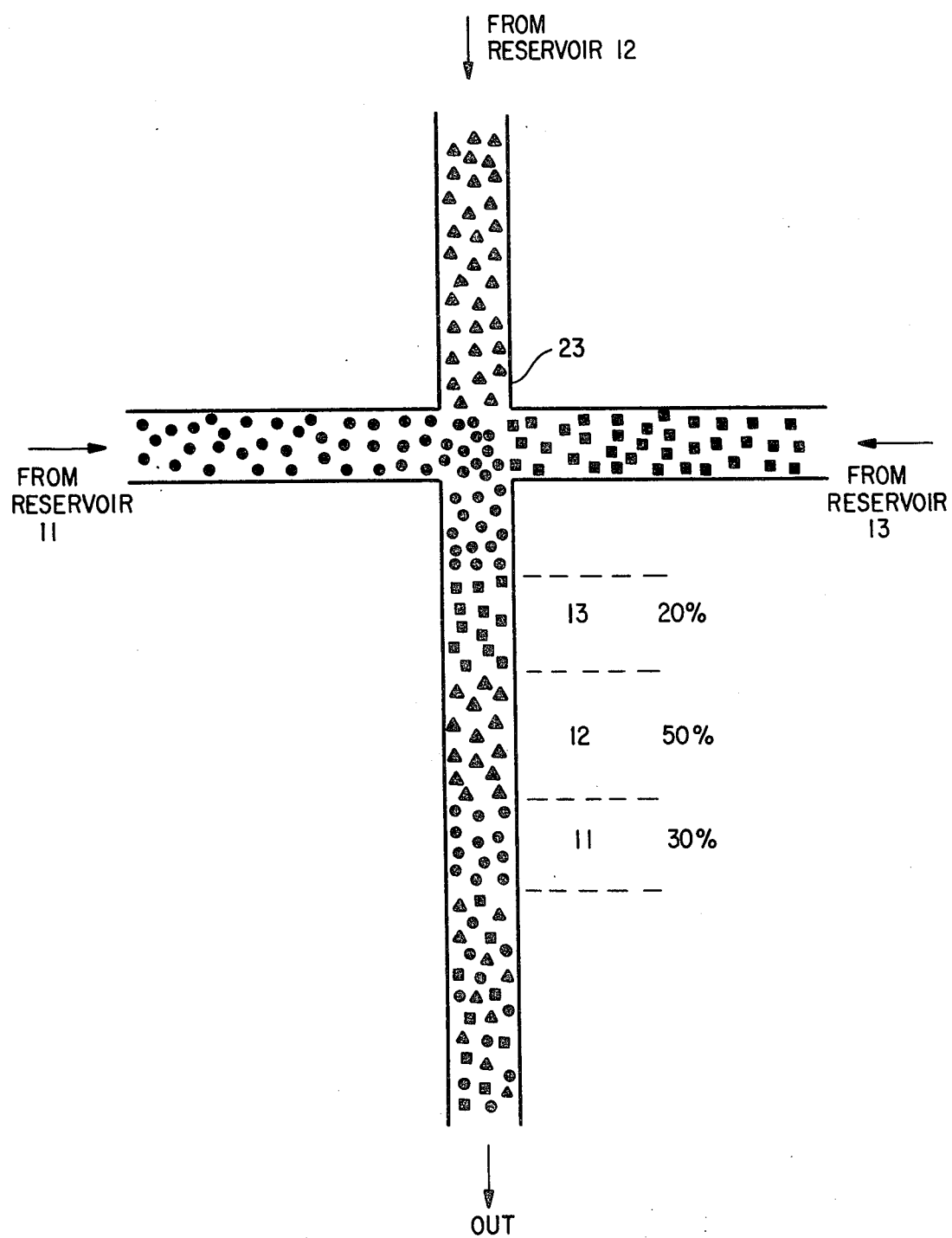

The time division metering system of the present invention will be made more clear by reference to the accompanying drawings wherein FIG. 1 is a schematic representation of the aforesaid metering system;

FIG. 2 is a schematic representation of the flow control pattern produced by one embodiment of the instant time division metering system; and FIG. 3 represents a diagramatic view of the fluid stream produced by the instant system in a blending mode.

Turning first to FIG. 1, a plurality of pressurized reservoir vessels 11, 12 and 13 are shown. It is to be understood that the number of reservoir vessels that can be employed in the practice of the present invention is not narrowly critical and any number from 2 to 20 or even more can be employed. The use of three vessels in this drawing is for convenience only and operation of these alternate numbers of reservoir vessels can be carried out by one skilled in the art in direct analogy to the description to be given below.

The pressure of the vessels is controlled in a manner known per se by use of a regulator 14 which is in operational contact with each of the reservoir vessels through a manifold means 15 and lines 16, 17 and 18. Pressure for the system is provided from a suitable fluid pressure source which is not shown but which can be a conventionally employed pressure source, i.e., gas line, gas cylinder, compressor or the like.

Each of the reservoir vessels contains an individual fluid which is to be metered into a common flow channel. An electronic controller 19 such as a multi-channel cycle timer is operatively connected to valves 20, 21 and 22 which control the flow from reservoir vessels 11, 12 and 13, respectively. The electronic controller 19 provides electrical signals which serve to open the three aforesaid valves in a predetermined sequence and for pre-determined intervals. In this manner the electronic controller serves to determine the total flow rate of fluid from each of the reservoir vessels into the desired end stream. By setting the controls on the electric controller means to any desired ratio, the pulses sent out to the valves are varied accordingly. For example, if it is desired that the ultimate flow stream contain 30% of the fluid from vessel 11, 50% of the fluid from vessel 12 and 20% of the fluid from vessel 13 in a one second flow cycle valve 20 would be initially opened for a period of 300 milliseconds and then closed, valve 21 would then be opened for a period of 500 milliseconds and then closed, and then valve 22 would be opened for 200 milliseconds and then closed. The process can then be repeated for as many cycles as desired at one second intervals. The time interval is not critical and can be selected to optimize operation by considering the number of channels in operation and/or flow rates utilized.

FIG. 2 shows the resulting flow from each of the reservoirs produced by operation of the invention according to the aforesaid embodiment. Thus in a one second cross section of the resulting sample stream the content thereof would comprise a volume equal to a 30% proportion of the fluid from reservoir 11, a 50% proportion of the fluid from reservoir 12, and a 20% proportion of the fluid from reservoir 13. For the purpose of convenience it is to be understood that the viscosity of the fluids being measured are considered to be essentially similar. However, in the event that extremely dissimilar viscosities are involved suitable compensation can be introduced into the system by use of flow restrictors in a manner known per se and/or by employing individual reservoir pressure regulators.

In the event that it is desired that the resulting flow stream be well mixed and a rapid clock rate does not provide enough intermixing of the fluids being provided from the respective reservoir vessels then a mixing tee 23 designed to have a high degree of turbulent flow can be provided. The flow rate in the interval volume of the connecting piping should be considered to select the appropriate clock frequency as to allow the small volumes of each reagent to intermix as shown in FIG. 3. As each discrete aliquot moves through the tubing, internal flow turbulence and diffusion intermix the fluids so that they are rapidly blended into a homogenous mixture.

In an alternative embodiment not herein depicted, it is possible to maintain the discreet pulse sequences of respective fluids by utilizing a tee for connecting the respective streams which tee is designed to minimize turbulent flow. In such embodiment it would also be possible to employ an inert, spacer fluid, i.e., air or inert gas bubbles to help preserve the integrity of each fluid sample. Such spacer fluids can be conveniently provided by utilizing one of the reservoir vessels within the system which can be integrated by appropriate timing of the electronic controller into the fluid flow from each of the other reservoir vessels. A separate valve connected to the pressurizing medium will also provide the same.

Pulses from the changes in flow can be eliminated with conventional pulse dampeners whenever necessary. However, in low pressure systems the capacitance of the interconnecting tubing generally dampens the pulses. The instant system can be utilized for blending virtually any mixture of fluids, either liquids or gases, with extremely high accuracy. In specific embodiments the instant system can be employed to provide reagents and buffers for a fluoresence monitor such as is described in U.S. Pat. Nos. 3,876,881, 3,892,530 or 3,892,532. Alternatively, by use of a computer controlled electronic control means it is possible to meter and alter at a programmed rate, changes in pH gradients with concentrated buffers which could be diluted and blended to any desired pH range and then employed in chromatographic systems.

I claim:

1. A time division metering system comprising in combination:
   A. a plurality of fluid reservoir vessel means each said vessel means being in operative fluid flow relationship with a valve means said valve means controlling the flow of fluid from said vessel means;
   B. electronic controller means in electronic control relationship with said plurality of valves wherein said electronic controller means provides a signal to each said valve means in preselected order, said signal causing each said valve means to open for a predetermined interval and at a predetermined frequency thereby allowing fluid to flow from the corresponding reservoir vessel means so as to achieve rapid cycling;
   C. tee means in operative fluid flow relation with each said valve means wherein the fluid flowing from said valve means are combined to form a single final fluid stream containing quantities of the respective fluids from said reservoir vessel means in exact ratio to the time intervals each corresponding valve means was held open.

2. The system of claim 1 wherein said fluid reservoir vessel means are pressurized.

3. The system of claim 2 wherein a single pressure regulator means controls the pressure of all said fluid reservoir vessel means.

4. The system of claim 1 wherein said tee means provides turbulent flow thereby blending said various fluids into a homogeneous single fluid stream.

5. The system of claim 1 wherein said tee means provides non-turbulent flow thereby maintaining each said fluid streams from said plurality of fluid reservoir vessel means as discrete portions of said final fluid stream.

6. The system of claim 5 wherein one of said fluid reservoir vessel means provides a spacer fluid to help maintain the integrity of said individual fluid streams.

7. The system of claim 6 wherein said spacer fluid is air and said individual fluid streams are liquids.

* * * * *